United States Patent
Ou et al.

(12)

(10) Patent No.: US 10,801,942 B2
(45) Date of Patent: Oct. 13, 2020

(54) MULTI-FUNCTIONAL MULTI-FIELD COUPLING SEEPAGE EXPERIMENT DEVICE AND TESTING METHOD THEREOF

(71) Applicant: SOUTHWEST PETROLEUM UNIVERSITY, Chengdu (CN)

(72) Inventors: Chenghua Ou, Chengdu (CN); Haiyan Zhu, Chengdu (CN); Qingyou Liu, Chengdu (CN); Chaochun Li, Chengdu (CN)

(73) Assignee: SOUTHWEST PETROLEUM UNIVERSITY, Chengdu (CN)

( * ) Notice: Subject to any disclaimer, the term of this patent is extended or adjusted under 35 U.S.C. 154(b) by 218 days.

(21) Appl. No.: 16/306,030

(22) PCT Filed: Sep. 6, 2017

(86) PCT No.: PCT/CN2017/100628
§ 371 (c)(1),
(2) Date: Nov. 30, 2018

(87) PCT Pub. No.: WO2019/033472
PCT Pub. Date: Feb. 21, 2019

(65) Prior Publication Data
US 2019/0234856 A1 Aug. 1, 2019

(30) Foreign Application Priority Data

Aug. 16, 2017 (CN) .......................... 2017 1 0702054

(51) Int. Cl.
| | |
|---|---|
| *G01N 15/08* | (2006.01) |
| *G01N 33/24* | (2006.01) |
| *E21B 49/02* | (2006.01) |

(52) U.S. Cl.
CPC ......... *G01N 15/082* (2013.01); *G01N 33/241* (2013.01); *E21B 49/02* (2013.01)

(58) Field of Classification Search
CPC ...... G01N 15/00; G01N 15/08; G01N 15/082; G01N 33/24; G01N 33/241; E21B 49/00; E21B 49/02
See application file for complete search history.

(56) References Cited

U.S. PATENT DOCUMENTS

| | | | |
|---|---|---|---|
| 5,493,226 A | * | 2/1996 | Honarpour ............ E21B 49/005 324/376 |
| 7,011,154 B2 | | 3/2006 | Maher et al. |
| 2018/0335374 A1 | * | 11/2018 | Kanj ..................... E21B 49/006 |

FOREIGN PATENT DOCUMENTS

| | | |
|---|---|---|
| CN | 103233704 A | 8/2013 |
| CN | 103616290 A | 3/2014 |
| CN | 102735548 B | 7/2014 |
| CN | 103278428 B | 5/2015 |

(Continued)

*Primary Examiner* — Nguyen Q. Ha
(74) *Attorney, Agent, or Firm* — Bayramoglu Law Offices LLC (57) ABSTRACT

A multi-functional multi-field coupling seepage experiment device includes a device body, a stress field control system, a temperature field control system, a fluid loading control system and a fluid seepage measurement system. The present invention further discloses seepage experiments performed on tight gas, shale gas, tight oil, shale oil, natural gas hydrate and geothermal heat in a multi-field coupling state of a temperature field, a stress field, a pore pressure field and a seepage field.

5 Claims, 3 Drawing Sheets

(56) References Cited

FOREIGN PATENT DOCUMENTS

| CN | 105403672 A | 3/2016 |
|----|-------------|--------|
| CN | 105628811 A | 6/2016 |
| CN | 106066291 A | 11/2016 |
| CN | 106093345 A | 11/2016 |
| CN | 104655495 B | 5/2017 |

\* cited by examiner

MULTI-FUNCTIONAL MULTI-FIELD COUPLING SEEPAGE EXPERIMENT DEVICE AND TESTING METHOD THEREOF

CROSS REFERENCE TO THE RELATED APPLICATIONS

This application is the national phase entry of International Application No. PCT/CN2017/100628, filed on Sep. 6, 2017, which claims priority to Chinese Patent Application 201710702054.6 filed on Aug. 16, 2017, the entire contents of which are incorporated herein by reference.

TECHNICAL FIELD

The invention relates to the field of oil and gas engineering, in particular to a multi-functional multi-field coupling seepage experiment device and a testing method thereof.

BACKGROUND

In recent years, with the in-depth development of the petroleum industry, the exploitation of unconventional energy sources such as tight gas, shale gas, tight oil, shale oil, natural gas hydrate, geothermal heat, etc. has received more and more attention, and has gradually become a hot spot for energy development in China. The above-mentioned unconventional energy sources involve large differences in fluid types, large differences in storage medium types and large differences in temperature ranges, and are all located in stress field environments formed by formation confining pressure and overburden pressure, thereby bringing huge challenge for the relevant seepage experiment device design and test methods.

The patent "Multi-functional True Triaxial Fluid-solid Coupling Test System" (Application No.: 201210231738.X) of Xujiang, et al. of Chongqing University completed the development of a fluid-solid coupling experiment system. However, this invention patent lacks a temperature loading and control system and cannot simulate a seepage experiment in a real formation environment. The experimental object is only limited to coalbed methane, and it is impossible to test seepage of shale gas, tight gas, shale oil, tight oil, natural gas hydrate and hot dry rock under real formation conditions.

The patent "A Coal-rock High-temperature High-pressure True Triaxial fracturing Seepage Experiment device" (Application No.: 201510080598.4) of Liang Weiguo, et al. of Taiyuan University of Technology completed an experiment device for seepage of coal and rock under stress and strain conditions of high-temperature rock. However, this experiment device lacks a low-temperature loading and control system and a liquid loading and seepage system, such that the experiment device cannot complete seepage experiments of natural gas hydrate, shale oil and tight oil.

The patent "Device and Method for Stress-Seepage-Temperature Coupling and Displacement Test of gas-bearing shale" (Application No: 201310172572.3) of Feng Xiating, Chen Tianyu, et al. of Northeastern University completed the design of a high temperature displacement device. However, this experiment device lacks a low-temperature loading and control system and a liquid loading and seepage system, such that the experiment device cannot complete seepage experiments of natural gas hydrate, shale oil and tight oil.

The patent "A Competitive Adsorption Test device for Supercritical $CO_2$ and $CH_4$ in shale and Testing Method Thereof" (Application Number: 2015109996370) of Pan Yi, et al. of Southwest Petroleum University completed the design of a competitive adsorption test device. However, this device lacks an axial compression loading system and cannot monitor and measure the dimensional changes of a rock sample in the radial and axial directions under the stress, so seepage experiments of shale gas, tight gas, shale oil, tight oil, natural gas hydrate and hot dry rock under a stress field cannot be completed.

For the multi-field coupling seepage test of tight gas, shale gas, tight oil, shale oil, natural gas hydrate and geothermal heat, the above patents have the following problems: (1) the internal conditions of a formation rock sample cannot be simulated realistically by using artificial cores; (2) the experimental functions are single, and each experiment object needs a set of special equipment for experiments for shale gas, or shale oil, or natural gas hydrate, or geothermal resource, so the test cost is high, the test period is long, and the equipment takes up a lot of space; (3) there is lacking of a device for exploring the changes in the physical properties of underground reservoirs under simulated three-dimensional stress conditions; (4) the needs of natural gas hydrate and geothermal seepage experiments for low and high temperature cannot be met.

In summary, the existing multi-field coupling seepage experiment equipment has relatively simple functions, and can only perform a multi-field coupling seepage experiment of single fluid, which is either multi-field coupling seepage of coalbed methane, multi-field coupling seepage of shale gas, or multi-field coupling seepage of tight gas, so it is impossible to use the same set of equipment to carry out multi-field coupling seepage experiments of shale gas, tight gas, shale gas, tight oil, shale oil, natural gas hydrate and geothermal heat respectively.

However, the seepage of shale gas, tight gas, shale oil, tight oil, natural gas hydrate, and hot dry rock in a real stratum environment occurs in coupling environments of a temperature field, a stress field, a pore pressure field and a gas and liquid seepage field. Therefore, the developed equipment must first establish the coupling environments of the above four fields. To adapt to seepage tests of shale gas, tight gas, shale oil, tight oil, natural gas hydrate and hot dry rock, it is also possible to establish high and low temperature control and measurement systems, gas and liquid loading and measurement systems, and chambers that are capable of sealing high pressure gases. Because not all of the above components are provided in the existing equipment, it is difficult to perform seepage tests of gas, liquid, high-heat fluid and low-temperature fluid at the same time, and it is also impossible to carry out seepage tests of shale gas, tight gas, shale oil, tight oil, natural gas hydrate and hot dry rock.

The tight oil and shale oil have a burial depth of 2 to 3 kilometers and a burial temperature of 60° C. to 90° C. respectively; the tight gas and shale gas have a burial depth of 2 to 4 kilometers, and a burial temperature of 60° C. to 120° C. respectively; the natural gas hydrate has a burial depth within 100 meters, and a burial temperature around minus 10° C.; the hot dry rock has a burial depth of 3 to 6 kilometers and a temperature range of 90° C. to 170° C.

Technical Problems

An objective of the present invention is to overcome the defects of the prior art and provide a multi-functional multi-field coupling seepage experiment device which is capable of performing exploitation seepage experiments of unconventional energy resources such as tight gas, shale gas, tight oil, shale oil, natural gas hydrate and geothermal heat under a multi-field coupling state of a temperature field, a stress field, a pore pressure field and a seepage field, and a testing method thereof.

SUMMARY

Said objective of the present invention is implemented by the following technical solutions: a multi-functional multi-field coupling seepage experiment device comprises a device body, a stress field control system, a temperature field control system, a fluid loading control system and a fluid seepage measurement system;

an experiment chamber in which a bearing platform, a rock sample, a pressure head, a metal washer, a heat shrinkable tube and a cold bath are provided is provided inside the device body; the bearing platform is provided inside the experiment chamber; the upper end and the lower end of the rock sample are provided with a temperature sensor respectively; an axial extensometer and a radial extensometer are provided on the rock sample; the rock sample is placed on the top of the bearing platform and sleeved with the heat shrinkable tube; the heat shrinkable tube is provided in the cold bath; the pressure head extends downward into the experiment chamber; a rubber ring and a metal washer are connected to the bottom of the pressure head in sequence; the metal washer is in contact with the top surface of the rock sample; an upper pipeline is provided on the metal washer; a port of the upper pipeline is in contact with the upper surface of the rock sample; a valve Vm located in the experiment chamber is connected to the upper pipeline; a lower pipeline is connected to the lower part of the device body; a valve Vx located in the experiment chamber is connected to the lower pipeline; a resistance wire is provided on the inner wall of the experiment chamber;

the stress field control system comprises a confining pressure hydraulic pump and an axial pressure hydraulic pump, wherein a valve Vj and a pressure gauge A are connected to an liquid outlet of the confining pressure hydraulic pump in sequence; the other end of the pressure gauge A is communicated with the experiment chamber; a valve Vk and a pressure gauge B are connected to a liquid outlet of the axial pressure hydraulic pump; the other end of the pressure gauge B is communicated with a hydraulic flow passage inside the pressure head;

the temperature field control system comprises an air conditioning oil refrigerator, a heating furnace and a thermometer A, wherein a valve Vi is connected to a cooling medium outlet end of the air conditioning oil refrigerator; the other end of the valve Vi is communicated with the cold bath; the heating furnace is connected with the resistance wire; the thermometer A is connected with the temperature sensor;

the fluid loading control system comprises a constant-flux pump, a first intermediate container, a second intermediate container, a third intermediate container and a fourth intermediate container, wherein a valve Va is connected between an outlet end of the constant-flux pump and each of the intermediate containers; a valve Vb, a valve Vc, a valve Vd and a valve Ve are connected to outlet ends of the first intermediate container, the second intermediate container, the third intermediate container and the fourth intermediate container respectively; a pressure gauge C is connected between each of the other ends of the valve Vb, the valve Vc, the valve Vd and the valve Ve and the valve Vx; a valve Vn and a vacuum pump are connected to a node between the pressure gauge C and the valve Vx in sequence;

the fluid seepage measurement system comprises a back pressure valve connected to the valve Vm, wherein the back pressure valve is connected with the valve Vm; two branches are connected to the other end of the valve Vm, wherein one branch consists of a valve Vf, a gas meter and a gas chromatograph which are connected in sequence; the other branch consists of a valve Vg, a gas-liquid separator, a liquid meter and a liquid chromatograph which are connected in sequence; a valve Vh is connected between the node between the gas meter and the valve Vf and the gas-liquid separator; a valve Vy is connected between an inlet end of the back pressure valve and an outlet end of the valve Vn.

The multi-functional multi-field coupling seepage experiment device further comprises a console that is connected with the axial extensometer, the radial extensometer, the air conditioning oil refrigerator and the heating furnace.

The device body comprises a base, a housing and a top cover, wherein the top cover and the base are fixedly connected to the upper end and the lower end of the housing respectively.

A back pressure pump is also connected to the back pressure valve.

A thermometer B is connected to an outlet of the back pressure valve.

A testing method for the multi-functional multi-field coupling seepage experiment device according to any of claims 1 to 4 comprises the following steps:

S1, a test of replacing tight gas or shale gas with carbon dioxide under multi-field coupling, which includes the following test steps:

(1), preparing a tight sandstone or shale rock sample to be tested; compounding tight gas or shale gas in a first intermediate container, compounding carbon dioxide in a second intermediate container, inspecting various components of the device and their connection relationships and adjusting them to initial working states;

(2), sleeving the rock sample to be tested with a heat shrinkable tube; installing a temperature sensor to the upper end and the lower end of the rock sample respectively; installing an axial extensometer and a radial extensometer on the rock sample; placing the rock sample on the top of a bearing platform; placing a metal washer and a rubber ring on the top of the rock sample in sequence, then connecting the rubber ring to a pressure head, and closing an experiment chamber;

(3), closing a valve Vb, a valve Vc, a valve Vd, a valve Ve, a valve Vm and a valve Vy; opening a valve Vn and a valve Vx; turning on a vacuum pump and a heating furnace; vacuumizing the experiment chamber by the vacuum pump to further vacuumize the rock sample; heating, by the heating furnace, the experiment chamber with a resistance wire to further heat the rock sample; forming a temperature field when a reading on a pressure gauge C is stable and a reading on a thermometer A is stable;

(4), turning off the vacuum pump and closing the valve Vn; opening the valve Va, the valve Vb and a constant-flux pump; pumping, by the constant-flux pump, the tight gas or shale gas in the first intermediate container into the experiment chamber through the valve Vb and the valve Vx in sequence to make the rock sample saturated, i.e., the rock sample is filled with gas, thereby forming a pore pressure field and a seepage field; opening a valve Vj and a valve Vk at the same time, and introducing hydraulic oil into the experiment chamber by a confining pressure hydraulic pump; applying, by the hydraulic oil, a radial pressure to the heat shrinkable tube and further a radial pressure to the rock sample; pumping hydraulic oil into a hydraulic flow passage of the pressure head by an axial pressure hydraulic pump; applying, by the pressure head, an axial force to the rock sample, till numerical values of a pressure gauge A, a pressure gauge B and a pressure gauge C reach experimentally set pressure values; turning off the hydraulic pump to form a stress field;

(5), observing the reading of the thermometer A; proceeding to the next step when a numerical value of the thermometer A is stabilized to an experimentally set numerical value;

(6), closing the valve Vb, opening the valve Vc, and pressurizing the constant-flux pump; pumping, by the constant-flux pump, the carbon carbonate in the second intermediate container into the experiment chamber through the valve Vc and the valve Vx in sequence; then closing the valve Vc and the valve Vx, and standing for a period of time;

(7), closing the valve Vg and the valve Vh after the gases in the experiment chamber are mixed sufficiently; opening the valve Vf, the valve Vm and the valve Vy, wherein the mixed gas in the experiment chamber flows out from the valve Vm according to a preset outlet pressure, and then is sprayed out from a back pressure valve; metering a volume of the gas by a gasometer, and then detecting components of the discharged gas with a gas chromatograph; during the experiment, automatically acquiring, by the axial extensometer and the radial extensometer, an axial deformation and a radial deformation of the rock sample, and transmitting the acquired data to a console;

(8), at the end of the experiment, recovering the tight sandstone or rock sample, sealing and stocking the unused high-purity experimental carbon dioxide, tight gas or shale gas; and restoring the device to a shutdown state;

S2, a test of displacing tight oil or shale oil with carbon dioxide under multi-field coupling, which includes the following test steps:

(1), preparing a tight sandstone or shale rock sample as a rock sample; compounding carbon dioxide in a fourth intermediate container, compounding tight oil or shale oil in a third intermediate container, inspecting various components of the device and their connection relationships and adjusting them to initial working states;

(2) repeating steps S1(2) to S1(3); then turning off the vacuum pump and closing the valve Vn; opening the valve Va, the valve Vd and the constant-flux pump; pumping, by the constant-flux pump, crude oil in the third intermediate container into the experiment chamber through the valve Vd and the valve Vx in sequence to make the rock sample saturated, i.e., the rock sample is filled with the tight oil or shale oil, thereby forming a pore pressure field and a seepage field; opening the valve Vj and the valve Vk at the same time, and introducing hydraulic oil into the experiment chamber by the confining pressure hydraulic pump; applying, by the hydraulic oil, a radial pressure to the heat shrinkable tube and further a radial pressure to the rock sample; pumping hydraulic oil to the hydraulic flow passage of the pressure head by the axial pressure hydraulic pump, such that the pressure head applies an axial force to the rock sample, till numerical values of the pressure gauge A, the pressure gauge B and the pressure gauge C reach experimentally set pressure values; turning off the hydraulic pump to form a stress field;

(3) repeating the step S1(5); then closing the valve Vd and the valve Vf, and opening the valve Ve, the valve Vg, the valve Vh and the valve Vm; pressurizing the constant-flux pump; pumping, by the constant-flux pump, the carbon dioxide in the fourth intermediate container into the experiment chamber through the valve Ve and the valve Vx in sequence;

(4) enabling testing fluid in the experiment chamber to flow out from the valve Vm and the back pressure valve according to a preset outlet pressure; after a gas-liquid mixture passes through a gas-liquid separator, metering a volume of gas by the gasometer when the gas enters the gasometer, and then detecting components of the discharged gas with a gas chromatograph; metering the volume of liquid by a liquid meter when the liquid enters the liquid meter, and detecting components of the liquid with a liquid chromatograph; during the experiment, automatically acquiring, by the axial extensometer and the radial extensometer, an axial deformation and a radial deformation of the rock sample, and transmitting the acquired data to a console;

(5) at the end of the experiment, recovering the tight sandstone or shale, sealing and stocking the unused high-purity experimental carbon dioxide, tight gas or shale oil; and restoring the device to a shutdown state;

S3, a test of exploitation efficiency by replacing hydrate with carbon dioxide under multi-field coupling, which includes the following steps:

(1), preparing a hydrate reservoir rock sample to be tested; placing methane in the first intermediate container, placing distilled water in the third intermediate container, and placing carbon dioxide in the fourth intermediate container; inspecting various components of the device and their connection relationships and adjusting them to initial working states;

(2) repeating the step S1(2); then closing the valve Vb, the valve Vc, the valve Vd, the valve Ve, the valve Vm and the valve Vy; opening the valve Vn, the valve Vi and the valve Vx; turning on the vacuum pump and an air conditioning oil refrigerator; vacuumizing the experiment chamber with the vacuum pump to further vacuumize the rock sample; pumping a cooling medium to a cold bath by the air conditioning oil refrigerator to refrigerate the experiment chamber, and further refrigerating the rock sample;

(3), when a numerical value displayed on the pressure gauge C is stable, turning off the vacuum pump, closing the valve Vn, and opening the valve Va, the valve Vb and the valve Vd; pumping, by the constant-flux pump, the methane in the first intermediate container into the experiment chamber through the valve Vb and the valve Vx in sequence, and meanwhile, pumping, by the constant-flux pump, the distilled water in the third intermediate container into the experiment chamber through the valve Vd and the valve Vx in sequence, such that the rock sample is saturated, i.e., the rock sample is filled with the methane and the distilled water; continuously cooling by the air conditioning oil refrigerator to form a stable low-temperature field; opening the valve Vj and the valve Vk at the same time; introducing, by the confining pressure hydraulic pump, hydraulic oil to the experiment chamber; applying, by the hydraulic oil, a radial pressure to the heat shrinkable tube and further a radial pressure to the rock sample; pumping, by the axial pressure hydraulic pump, hydraulic oil into the flow passage of the pressure head, such that the pressure head applies an axial force to the rock sample, till the numerical values on the pressure gauge A, the pressure gauge B, and the pressure gauge C reach the experimentally set pressure values; maintaining the set pressure values to form a stable stress field and a pore pressure field;

(4) repeating the step S1(5); after stable natural gas hydrate is formed inside the experiment chamber, closing the valve Vb and the valve Vd; pumping, by the constant-flux pump, the carbon dioxide in the fourth intermediate container into the experiment chamber through the valve Ve and the valve Vm in sequence; introducing a sufficient amount of carbon dioxide, and then closing the valve Va, the valve Ve and the valve Vx; standing the experiment chamber for a period of time;

(5), closing the valve Vf, and opening the valve Ve, the valve Vg, the valve Vh and the valve Vm; setting a pressure of the back pressure valve; enabling testing fluid in the experiment chamber to flow out from the valve Vm and the back pressure valve according to a preset outlet pressure; after a gas-liquid mixture passes through the gas-liquid separator, metering a volume of gas by the gasometer when the gas enters the gasometer, and then detecting components of the discharged gas with a gas chromatograph; metering the volume of liquid by a liquid meter when the liquid enters the liquid meter, and detecting components of the liquid with a liquid chromatograph; during the experiment, automatically acquiring, by the axial extensometer and the radial extensometer, an axial deformation and a radial deformation of the rock sample, and transmitting the acquired data to a console;

(6), at the end of the experiment, recovering the hydrate reservoir rock sample, sealing and stocking the unused experimental carbon dioxide, methane gas or distilled water; and restoring the device to a shutdown state;

S4, a test of heat exchange efficiency of geothermal heat under multi-field coupling, which includes the following steps:

(1), preparing a hot dry rock sample to be tested; compounding formation water in the third intermediate container; inspecting various components of the device and their connection relationships and adjusting them to initial working states;

(2), repeating the steps S1(2) to S1(3) to form a stable temperature field; then, opening the valve Vj and the valve Vk; applying, by the confining hydraulic pump, a radial force to hot dry rock, and applying, by the axial pressure hydraulic pump, an axial pressure to the hot dry rock; when the readings on the pressure gauge A, the pressure gauge B and the pressure gauge C reach stable values, forming a stable stress field; then, turning off the vacuum pump and the valve Vn, and opening the valve Va and the valve Vd; pumping, by the constant-flux pump, the formation water in the third intermediate container into the hot dry rock through the valve Vd and the valve Vx in sequence;

(3), opening the valve Vm, and closing the valve Vf and the valve Vh; enabling the formation water to flow out from the back pressure valve and to enter the liquid meter; metering the volume of the distilled water by the liquid meter; metering, by a thermometer C(39), the temperature of the formation water at the inlet end; metering, by a thermometer B, the temperature of the flowing-out formation water;

(4), during the experiment process, automatically acquiring an axial deformation or a radial deformation of the hot dry rock by extensometers;

(5), at the end of the experiment, recovering the hot dry rock, sealing and stocking the unused formation water; and restoring the device to a shutdown state.

Beneficial Effects

The present invention has the following advantages: (1) a complete set of experiment devices is established to meet the needs of compact gas, shale gas, tight oil, shale oil, natural gas hydrate and geothermal heat under complex formation conditions; (2) the loading test of a wide range of axial pressure and confining pressure is realized to complete the temperature change of a wide area, the temperature and pressure needs of the tight gas, the shale gas, the tight oil and the shale oil are met, and more importantly, the high temperature need of geothermal heat exploitation can be met while the low temperature need of a natural gas hydrate flow test is met; (3) a real stratum environment is simulated, and the exploitation seepage experiments of unconventional energy resources such as the tight gas, the shale gas, the tight oil, the shale oil, the natural gas hydrate and hot dry rock can be completed respectively by using the same equipment.

BRIEF DESCRIPTION OF THE DRAWINGS

in drawings, reference symbols represent the following components: 1—experiment chamber, 2—bearing platform, 3—rock sample, 4—pressure head, 5—metal washer, 6—heat shrinkable tube, 7—cool bath, 8—resistance wire, 9—confining pressure hydraulic pump, 10—axial pressure hydraulic pump, 11—pressure gauge A, 12—pressure gauge B, 13—air conditioning oil refrigerator, 14—heating furnace, 15—thermometer A, 16—constant-flow pump, 17—first intermediate container, 18—second intermediate container, 19—third intermediate container, 20—fourth intermediate container, 21—pressure gauge C, 22—vacuum pump, 23—back pressure valve, 25—gasometer, 26—gas chromatograph, 27—gas-liquid separator, 28—liquid meter, 29—liquid chromatograph, 30—console, 31—base, 32—housing, 33—top cover, 34—back pressure pump, 35—thermometer B, 36—temperature sensor, 37—axial extensometer, 38—radial extensometer.

DETAILED DESCRIPTION OF THE EMBODIMENTS

The present invention will be further described below in conjunction with the accompanying drawings, and the protection scope of the present invention is not limited to the followings.

Figure 1:
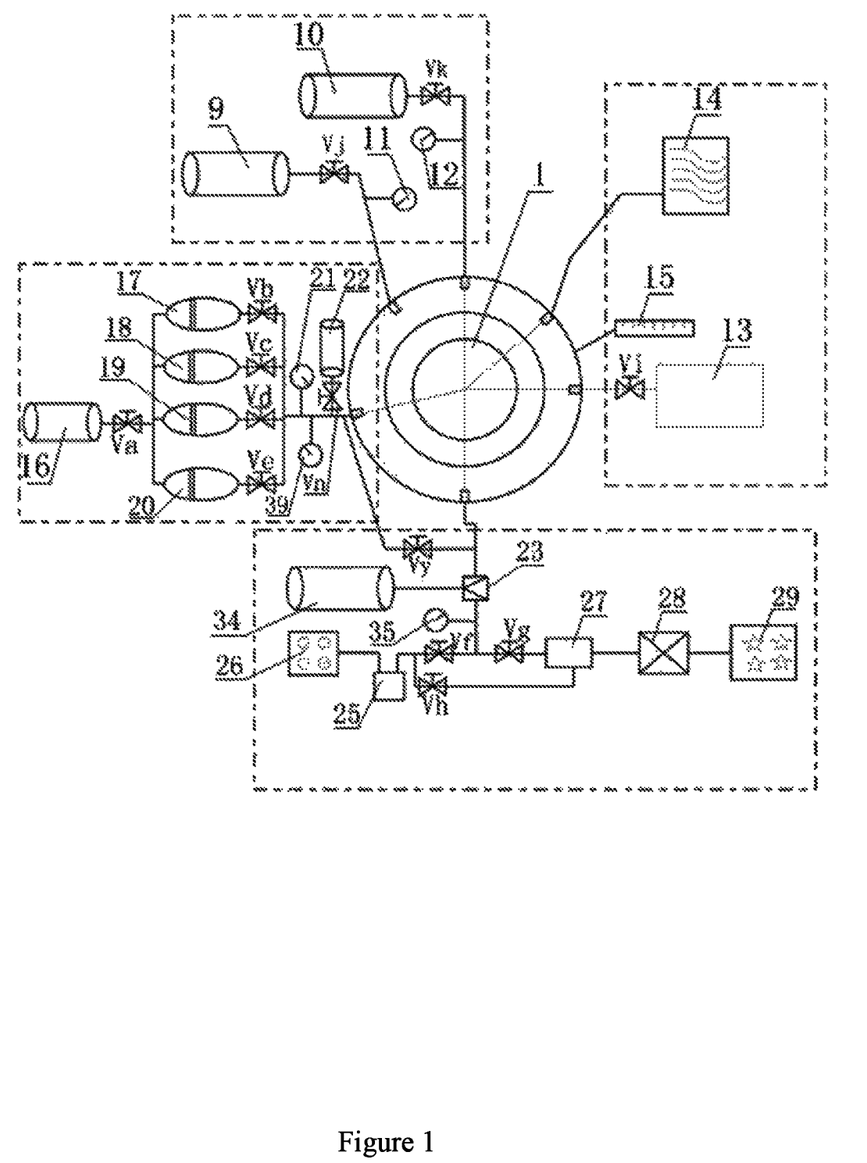
FIG. 1 is a schematic structural diagram of the present invention.
Figure 2:
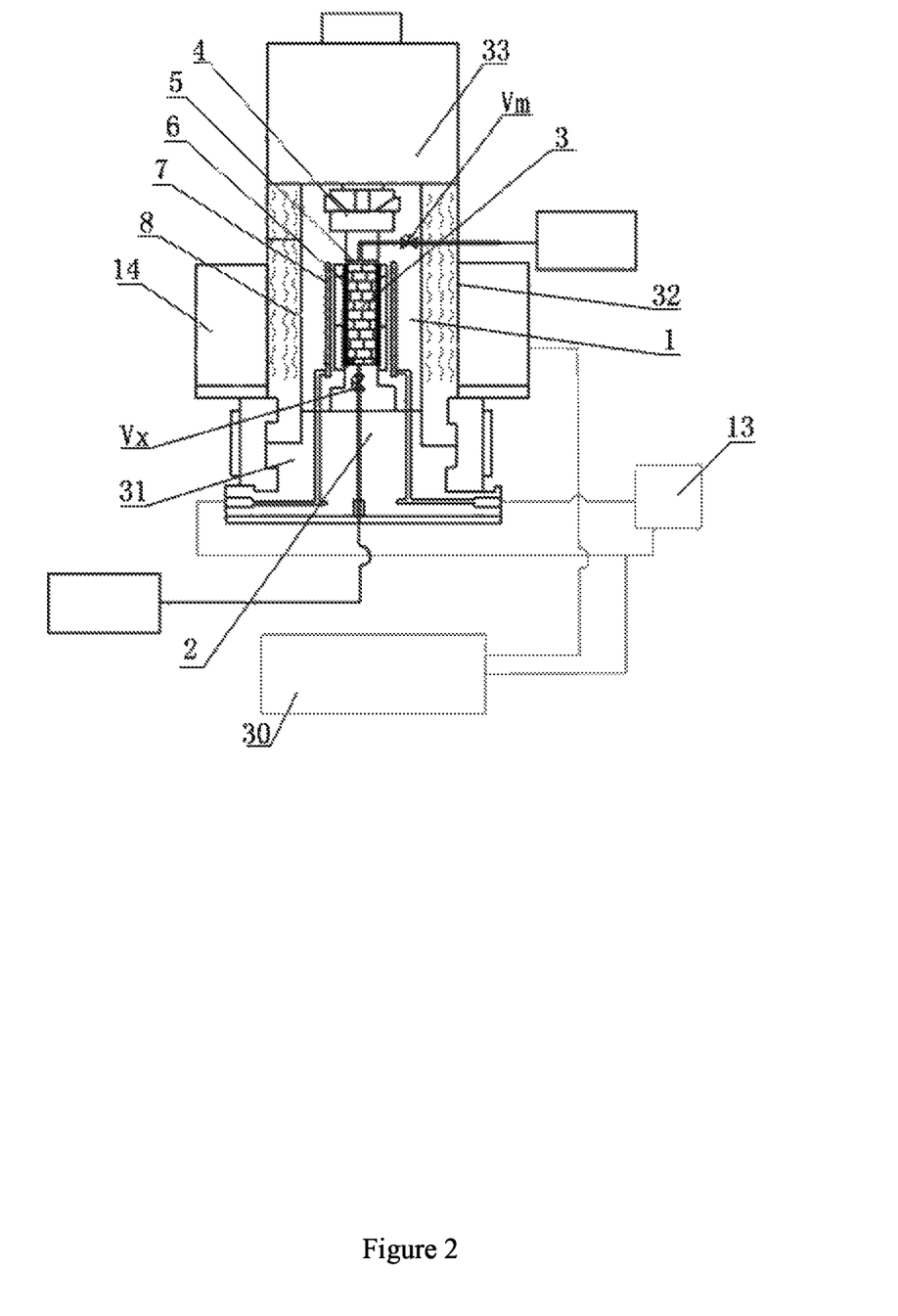
FIG. 2 is a schematic structural diagram of a device body.
Figure 3:
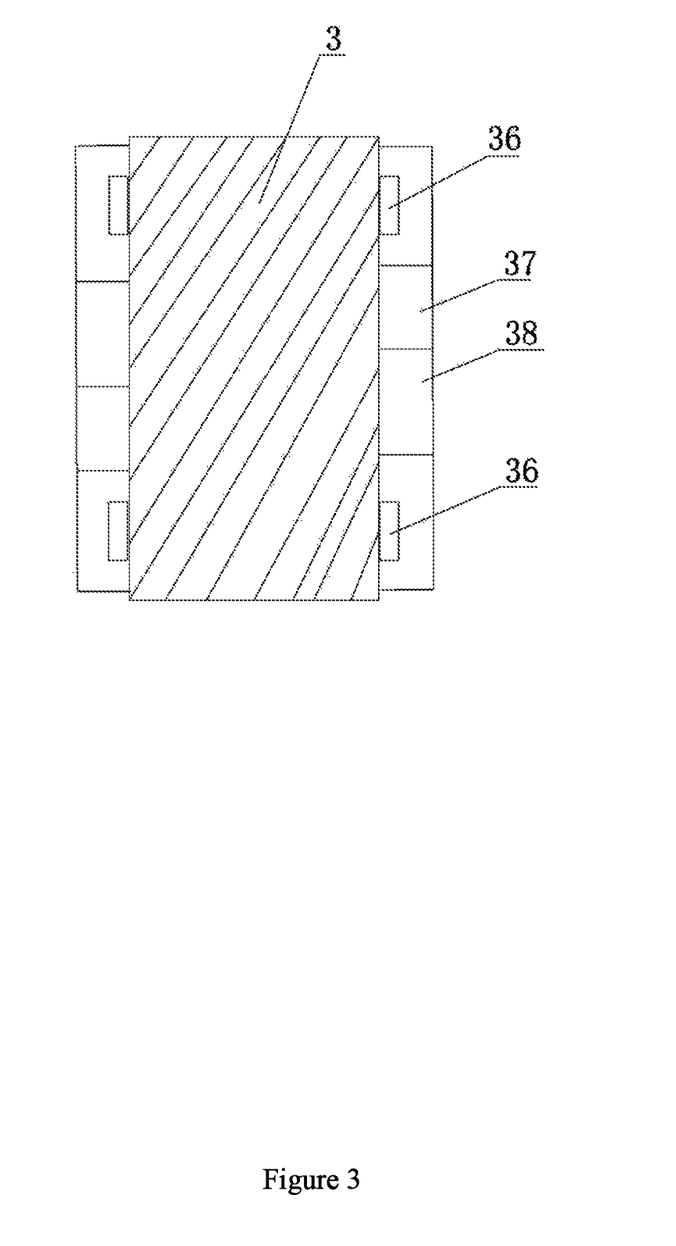
FIG. 3 is a schematic structural diagram of an extensometer and a temperature sensor installed on a rock sample.

As shown in FIGS. 1 to 2, a multi-functional multi-field coupling seepage experiment device comprises a device body, a stress field control system, a temperature field control system, a fluid loading control system and a fluid seepage measurement system.

An experiment chamber 1 in which a bearing platform 2, a rock sample 3, a pressure head 4, a metal washer 5, a heat shrinkable tube 6 and a cold bath 7 are provided is provided inside the device body; the bearing platform 2 is provided inside the experiment chamber 1; the upper end and the lower end of the rock sample 3 are provided with a temperature sensor respectively; an axial extensometer and a radial extensometer are provided on the rock sample 3; the rock sample 3 is placed on the top of the bearing platform 2 and sleeved with the heat shrinkable tube 6; the heat shrinkable tube 6 is provided in the cold bath 7; the pressure head 4 extends downward into the experiment chamber 1; a rubber ring and a metal washer 5 are connected to the bottom of the pressure head 4 in sequence; the metal washer 5 is in contact with the top surface of the rock sample 3; an upper pipeline is provided on the metal washer 5; a port of the upper pipeline is in contact with the upper surface of the rock sample 3; a valve Vm located in the experiment chamber 1 is connected to the upper pipeline; a lower pipeline is connected to the lower part of the device body; a valve Vx located in the experiment chamber 1 is connected to the lower pipeline; a resistance wire 8 is provided on the inner wall of the experiment chamber 1;

the stress field control system comprises a confining pressure hydraulic pump 9 and an axial pressure hydraulic pump 10, wherein a valve Vj and a pressure gauge A11 are connected to a liquid outlet of the confining pressure hydraulic pump 9 in sequence; the other end of the pressure gauge A11 is communicated with the experiment chamber 1; a valve Vk and a pressure gauge B12 are connected to a liquid outlet of the axial pressure hydraulic pump 10; the other end of the pressure gauge B12 is communicated with a hydraulic flow passage inside the pressure head 4;

the temperature field control system comprises an air conditioning oil refrigerator 13, a heating furnace 14 and a thermometer A15, wherein a valve Vi is connected to a cooling medium outlet end of the air conditioning oil refrigerator 13; the other end of the valve Vi is communicated with the cold bath 7; the heating furnace 14 is connected with the resistance wire 8; the thermometer A15 is connected with the temperature sensor;

the fluid loading control system comprises a constant-flux pump 16, a first intermediate container 17, a second intermediate container 18, a third intermediate container 19, and a fourth intermediate container 20, wherein a valve Va is connected between an outlet end of the constant-flux pump 16 and each of the intermediate containers; a valve Vb, a valve Vc, a valve Vd and a valve Ve are connected to outlet ends of the first intermediate container 17, the second intermediate container 18, the third intermediate container 19 and the fourth intermediate container 20 respectively; a pressure gauge C21 is connected between each of the other ends of the valve Vb, the valve Vc, the valve Vd and the valve Ve and the valve Vx; a valve Vn and a vacuum pump 22 are connected to a node between the pressure gauge C21 and the valve Vx in sequence;

the fluid seepage measurement system comprises a back pressure valve 23 connected to the valve Vm, wherein the back pressure valve 23 is connected with the valve Vm; two branches are connected to the other end of the valve Vm, wherein one branch consists of a valve Vf, a gas meter 25 and a gas chromatograph 26 which are connected in sequence; the other branch consists of a valve Vg, a gas-liquid separator 27, a liquid meter 28 and a liquid chromatograph 29 which are connected in sequence; a valve Vh is connected between the node between the gas meter 25 and the valve Vf and the gas-liquid separator 27; a valve Vy is connected between an inlet end of the back pressure valve 23 and an outlet end of the valve Vn.

The multi-functional multi-field coupling seepage experiment device further comprises a console 30 that is connected with the axial extensometer, the radial extensometer, the air conditioning oil refrigerator 13 and the heating furnace 14.

The device body comprises a base 31, a housing 32 and a top cover 33, wherein the top cover 33 and the base 31 are fixedly connected to the upper end and the lower end of the housing 32 respectively. A back pressure pump 34 is also connected to the back pressure valve 23. A thermometer B35 is connected to an outlet of the back pressure valve 23. A thermometer C(39) is connected between the pressure gauge C21 and the vacuum pump 22.

A testing method for the multi-functional multi-field coupling seepage experiment device comprises the following steps:

S1, a test of replacing tight gas or shale gas with carbon dioxide under multi-field coupling, which includes the following test steps:

(1), preparing a tight sandstone or shale rock sample to be tested; compounding tight gas or shale gas in a first intermediate container 17, compounding carbon dioxide in a second intermediate container 18, inspecting various components of the device and their connection relationships and adjusting them to initial working states;

(2), sleeving the rock sample to be tested with a heat shrinkable tube 6; installing a temperature sensor to the upper end and the lower end of the rock sample respectively; installing an axial extensometer and a radial extensometer on the rock sample; placing the rock sample on the top of a bearing platform 2; placing a metal washer 5 and a rubber ring on the top of the rock sample in sequence, then connecting the rubber ring to a pressure head 4 and closing an experiment chamber;

(3), closing a valve Vb, a valve Vc, a valve Vd, a valve Ve, a valve Vm and a valve Vy; opening a valve Vn and a valve Vx; turning on a vacuum pump 22 and a heating furnace 14; vacuumizing the experiment chamber 1 by the vacuum pump 22 to further vacuumize the rock sample; heating, by the heating furnace 14, the experiment chamber 1 with a resistance wire 8 to further heat the rock sample; forming a temperature field when a reading on a pressure gauge C21 is stable and a reading on a thermometer A15 is stable;

(4), turning off the vacuum pump 22 and closing the valve Vn, and opening the valve Va, the valve Vb and a constant-flux pump 16; pumping, the constant-flux pump 16, the tight gas or shale gas in the first intermediate container 17 into the experiment chamber 1 through the valve Vb and the valve Vx in sequence to make the rock sample saturated, i.e., the rock sample is filled with gas, thereby forming a pore pressure field and a seepage field; opening a valve Vj and a valve Vk at the same time, and introducing hydraulic oil into the experiment chamber 1 by a confining pressure hydraulic pump 9; applying, by the hydraulic oil, a radial pressure to the heat shrinkable tube 6 and further a radial pressure to the rock sample; pumping hydraulic oil to a hydraulic flow passage of the pressure head 4 by an axial pressure hydraulic pump 10, such that the pressure head 4 applies an axial force to the rock sample, till numerical values of a pressure gauge A11, a pressure gauge B12 and a pressure gauge C21 reach experimentally set pressure values; turning off the hydraulic pump to form a stress field;

(5), observing the reading of the thermometer A15; proceeding to the next step when a numerical value of the thermometer A15 is stabilized to an experimentally set numerical value;

(6), closing the valve Vb, opening the valve Vc, and pressurizing the constant-flux pump 16; pumping, by the constant-flux pump 16, the carbon carbonate in the second intermediate container 18 into the experiment chamber 1 through the valve Vc and the valve Vx in sequence; then closing the valve Vc and the valve Vx, and standing for a period of time;

(7), closing the valve Vg and the valve Vh after the gases in the experiment chamber 1 are mixed sufficiently; opening the valve Vf, the valve Vm and the valve Vy, wherein the mixed gas in the experiment chamber flows out from the valve Vm according to a preset outlet pressure, and then is sprayed out from a back pressure valve 23; metering a volume of the gas by a gasometer 25, and then detecting components of the discharged gas with a gas chromatograph 26, detecting mass fractions of carbon dioxide and methane gas, and analyzing a proportion of the methane gas to the carbon dioxide; during the experiment, automatically acquiring, by the axial extensometer and the radial extensometer, an axial deformation and a radial deformation of the rock sample, and transmitting the acquired data to a console 30;

(8), at the end of the experiment, recovering the tight sandstone or rock sample, sealing and stocking the unused high-purity experimental carbon dioxide, tight gas or shale gas; and restoring the device to a shutdown state;

S2, a test of displacing tight oil or shale oil with carbon dioxide under multi-field coupling, which includes the following test steps:

(1), preparing a tight sandstone or shale rock sample as a rock sample; compounding carbon dioxide in a fourth intermediate container 20, compounding tight oil or shale oil in a third intermediate container 19, inspecting various components of the device and their connection relationships and adjusting them to initial working states;

(2) repeating steps S1(2) to S1(3); then turning off the vacuum pump 22 and closing the valve Vn, and opening the valve Va, the valve Vd and the constant-flux pump 16; pumping, by the constant-flux pump 16, crude oil in the third intermediate container 19 into the experiment chamber 1 through the valve Vd and the valve Vx in sequence to make the rock sample saturated, i.e., the rock sample is filled with the tight oil or shale oil, thereby forming a pore pressure field and a seepage field; opening the valve Vj and the valve Vk at the same time, and introducing hydraulic oil into the experiment chamber 1 by the confining pressure hydraulic pump 9; applying, by the hydraulic oil, a radial pressure to the heat shrinkable tube 6 and further a radial pressure to the rock sample; pumping hydraulic oil to the hydraulic flow passage of the pressure head 4 by the axial pressure hydraulic pump 10, such that the pressure head 4 applies an axial force to the rock sample, till numerical values of the pressure gauge A11, the pressure gauge B12 and the pressure gauge C21 reach experimentally set pressure values; turning off the hydraulic pump to form a stress field;

(3) repeating the step S1(5); then closing the valve Vd and the valve Vf, and opening the valve Ve, the valve Vg, the valve Vh and the valve Vm; pressurizing the constant-flux pump 16; pumping, by the constant-flux pump 16, the carbon dioxide in the fourth intermediate container 20 into the experiment chamber 1 through the valve Ve and the valve Vx in sequence;

(4) enabling testing fluid in the experiment chamber to flow out from the valve Vm and the back pressure valve 23 according to a preset outlet pressure; after a gas-liquid mixture passes through a gas-liquid separator 27, metering a volume of gas by the gasometer 25 when the gas enters the gasometer 25, and then detecting components of the discharged gas with a gas chromatograph 26; metering the volume of liquid by a liquid meter 28 when the liquid enters the liquid meter 28, and detecting components of the liquid with a liquid chromatograph 29, and detecting non-hydrocarbon components, such as carbon, nitrogen and sulfur, as well as C1 to C20+alkane, naphthene and aromatic hydrocarbon components, and mass fractions thereof; during the experiment, automatically acquiring, by the axial extensometer and the radial extensometer, an axial deformation and a radial deformation of the rock sample, and transmitting the acquired data to a console 30;

(5) at the end of the experiment, recovering the tight sandstone or shale, sealing and stocking the unused high-purity experimental carbon dioxide, tight oil or shale oil; and restoring the device to a shutdown state;

S3, a test of exploitation efficiency by replacing hydrate with carbon dioxide under multi-field coupling, which includes the following steps:

(1), preparing a hydrate reservoir rock sample to be tested; placing methane in the first intermediate container 17, placing distilled water in the third intermediate container 19, and placing carbon dioxide in the fourth intermediate container 20; inspecting various components of the device and their connection relationships and adjusting them to initial working states;

(2) repeating the step S1(2); then closing the valve Vb, the valve Vc, the valve Vd, the valve Ve, the valve Vm and the valve Vy; opening the valve Vn, the valve Vi and the valve Vx; turning on the vacuum pump 22 and an air conditioning oil refrigerator 13; vacuumizing the experiment chamber 1 with the vacuum pump 22 to further vacuumize the rock sample; pumping a cooling medium to a cold bath 17 by the air conditioning oil refrigerator 13 to refrigerate the experiment chamber 1, and further refrigerating the rock sample;

(3), when a numerical value displayed on the pressure gauge C21 is stable, turning off the vacuum pump 22, closing the valve Vn, and opening the valve Va, the valve Vb and the valve Vd; pumping, by the constant-flux pump 16, the methane in the first intermediate container 17 into the experiment chamber 1 through the valve Vb and the valve Vx in sequence, and meanwhile, pumping, by the constant-flux pump 16, the distilled water in the third intermediate container 19 into the experiment chamber 1 through the valve Vd and the valve Vx in sequence, such that the rock sample is saturated, i.e., the rock sample is filled with the methane and the distilled water; continuously cooling by the air conditioning oil refrigerator to form a stable low-temperature field; opening the valve Vj and the valve Vk at the same time; introducing, by the confining pressure hydraulic pump 9, hydraulic oil to the experiment chamber 1; applying, by the hydraulic oil, a radial pressure to the heat shrinkable tube 6 and further a radial pressure to the rock sample; pumping, by the axial pressure hydraulic pump 10, the hydraulic oil to the flow passage of the pressure head 4, such that the pressure head 4 applies an axial force to the rock sample, till the numerical values on the pressure gauge A11, the pressure gauge B12, and the pressure gauge C21 reach the experimentally set pressure values; maintaining the set pressure values to form a stable stress field and a pore pressure field;

(4) repeating the step S1(5); after stable natural gas hydrate is formed inside the experiment chamber, closing the valve Vb and the valve Vd; pumping, by the constant-flux pump 16, the carbon dioxide in the fourth intermediate container 20 into the experiment chamber 1 through the valve Ve and the valve Vm in sequence; introducing a sufficient amount of carbon dioxide, and then closing the valve Va, the valve Ve and the valve Vx; standing the experiment chamber for a period of time;

(5), closing the valve Vf, and opening the valve Ve, the valve Vg, the valve Vh and the valve Vm; setting a pressure of the back pressure valve 23; enabling testing fluid to flow out from the valve Vm and the back pressure valve 23 according to a preset outlet pressure; after a gas-liquid mixture enters a gas-liquid separator 27, metering a volume of gas by the gasometer 25 when the gas enters the gasometer 25, and then detecting components of the discharged gas with a gas chromatograph 26; metering the volume of liquid by a liquid meter 28 when the liquid enters the liquid meter 28, and detecting components of the liquid with a liquid chromatograph 29, and detecting non-hydrocarbon components, such as carbon, nitrogen and sulfur, as well as C1 to C20+alkane, naphthene and aromatic hydrocarbon components and mass fractions thereof; during the experiment, automatically acquiring, the axial extensometer and the radial extensometer, an axial deformation and a radial deformation of the rock sample, and transmitting the acquired data to a console 30;

(6), at the end of the experiment, recovering the hydrate reservoir rock ample, sealing and stocking the unused experimental carbon dioxide, methane gas or distilled water; and restoring the device to a shutdown state;

S4, a test of heat exchange efficiency of geothermal heat under multi-field coupling, which includes the following steps:

(1), preparing a hot dry rock sample to be tested; compounding formation water in the third intermediate container 19; inspecting various components of the device and their connection relationships and adjusting them to initial working states;

(2), repeating the steps S1(2) to S1(3) to form a stable temperature field; then, opening the valve Vj and the valve Vk; applying, by the confining hydraulic pump 9, a radial force to hot dry rock, and applying, by the axial pressure hydraulic pump 10, an axial pressure to the hot dry rock; when the readings on the pressure gauge A11, the pressure gauge B12 and the pressure gauge C21 reach stable values, forming a stable stress field; then, turning off the vacuum pump 22 and the valve Vn, and opening the valve Va and the valve Vd; pumping, by the constant-flux pump 16, the formation water in the third intermediate container 19 into the hot dry rock through the valve Vd and the valve Vx in sequence;

(3), opening the valve Vm, and closing the valve Vf and the valve Vh; enabling the formation water to flow out from the back pressure valve 23 and to enter the liquid meter; metering the volume of the distilled water by the liquid meter 28; metering, by a thermometer C(39), the temperature of the formation water at the inlet end; metering, by a thermometer B35, the temperature of the flowing-out formation water;

(4), during the experiment process, automatically acquiring an axial deformation or a radial deformation of the hot dry rock by extensometers;

(5), at the end of the experiment, recovering the hot dry rock, sealing and stocking the unused formation water; and restoring the device to a shutdown state.

What is claimed is:

1. A multi-functional multi-field coupling seepage experiment device, comprising a device body, a stress field control system, a temperature field control system, a fluid loading control system and a fluid seepage measurement system;

an experiment chamber; a bearing platform, a rock sample, a pressure head, a metal washer, a heat shrinkable tube and a cold bath are provided inside the device body; the bearing platform is provided inside the experiment chamber; an upper end and a lower end of the rock sample are provided with a temperature sensor respectively; an axial extensometer and a radial extensometer are provided on the rock sample; the rock sample is placed on the top of the bearing platform and sleeved with the heat shrinkable tube; the heat shrinkable tube is provided in the cold bath; the pressure head extends downward into the experiment chamber; a rubber ring and the metal washer are connected to the bottom of the pressure head in sequence; the metal washer is in contact with the top surface of the rock sample; an upper pipeline is provided on the metal washer; a port of the upper pipeline is in contact with the upper surface of the rock sample; a valve Vm located in the experiment chamber is connected to the upper pipeline; a lower pipeline is connected to the lower part of the device body; a valve Vx located in the experiment chamber is connected to the lower pipeline; a resistance wire is provided on the inner wall of the experiment chamber;

the stress field control system comprises a confining pressure hydraulic pump and an axial pressure hydraulic pump, wherein a valve Vj and a pressure gauge A are connected to a liquid outlet of the confining pressure hydraulic pump in sequence; the other end of the pressure gauge A is communicated with the experiment chamber; a valve Vk and a pressure gauge B are connected to a liquid outlet of the axial pressure hydraulic pump; the other end of the pressure gauge B is communicated with a hydraulic flow passage inside the pressure head;

the temperature field control system comprises an air conditioning oil refrigerator, a heating furnace and a thermometer A, wherein a valve Vi is connected to a cooling medium outlet end of the air conditioning oil refrigerator; the other end of the valve Vi is communicated with the cold bath; the heating furnace is connected with the resistance wire; the thermometer A is connected with the temperature sensor;

the fluid loading control system comprises a constant-flux pump, a first intermediate container, a second intermediate container, a third intermediate container and a fourth intermediate container, wherein a valve Va is connected between an outlet end of the constant-flux pump and each of the intermediate containers; a valve Vb, a valve Vc, a valve Vd and a valve Ve are connected to outlet ends of the first intermediate container, the second intermediate container, the third intermediate container and the fourth intermediate container respectively; a pressure gauge C is connected between each of the other ends of the valve Vb, the valve Vc, the valve Vd and the valve Ve and the valve Vx; a valve Vn and a vacuum pump are connected to a node between the pressure gauge C and the valve Vx in sequence;

the fluid seepage measurement system comprises a back pressure valve connected to the valve Vm, wherein the back pressure valve is connected with the valve Vm; two branches are connected to the other end of the valve Vm, wherein one branch consists of a valve Vf, a gas meter and a gas chromatograph connected in sequence; the other branch consists of a valve Vg, a gas-liquid separator, a liquid meter and a liquid chromatograph connected in sequence; a valve Vh is connected between the node between the gas meter and the valve Vf and the gas-liquid separator; a valve Vy is connected between an inlet end of the back pressure valve and an outlet end of the valve Vn;

the multi-functional multi-field coupling seepage experiment device further comprises a console that is connected with the axial extensometer, the radial extensometer, the air conditioning oil refrigerator and the heating furnace.

2. The multi-functional multi-field coupling seepage experiment device according to claim 1, wherein the device body comprises a base, a housing and a top cover, wherein the top cover and the base are fixedly connected to the upper end and the lower end of the housing respectively.

3. The multi-functional multi-field coupling seepage experiment device according to claim 1, wherein a back pressure pump is connected to the back pressure valve.

4. The multi-functional multi-field coupling seepage experiment device according to claim 1, wherein a thermometer B is connected to an outlet of the back pressure valve.

5. A testing method for the multi-functional multi-field coupling seepage experiment device according to claim 1, comprising the following steps:
S1, a test of replacing tight gas or shale gas with carbon dioxide under multi-field coupling, which includes the following test steps:
S1(1), preparing a tight sandstone or shale rock sample to be tested; compounding tight gas or shale gas in a first intermediate container, compounding carbon dioxide in a second intermediate container, inspecting various components of the device and their connection relationships and adjusting them to initial working states;
S1(2), sleeving the rock sample to be tested with a heat shrinkable tube; installing a temperature sensor to the upper end and the lower end of the rock sample respectively; installing an axial extensometer and a radial extensometer on the rock sample; placing the rock sample on the top of a bearing platform; placing a metal washer and a rubber ring on the top of the rock sample in sequence, then connecting the rubber ring to a pressure head, and closing an experiment chamber;
S1(3), closing a valve Vb, a valve Vc, a valve Vd, a valve Ve, a valve Vm and a valve Vy; opening a valve Vn and a valve Vx; turning on a vacuum pump and a heating furnace; vacuumizing the experiment chamber by the vacuum pump to further vacuumize the rock sample; heating, by the heating furnace, the experiment chamber with a resistance wire to further heat the rock sample; forming a temperature field when a reading on a pressure gauge C is stable and a reading on a thermometer A is stable;
S1(4), turning off the vacuum pump and closing the valve Vn; opening the valve Va, the valve Vb and a constant-flux pump; pumping, by the constant-flux pump, the tight gas or shale gas in the first intermediate container into the experiment chamber through the valve Vb and the valve Vx in sequence to make the rock sample saturated, wherein, the rock sample is filled with gas, thereby forming a pore pressure field and a seepage field; opening a valve Vj and a valve Vk at the same time, and introducing hydraulic oil into the experiment chamber by a confining pressure hydraulic pump; applying, by the hydraulic oil, a radial pressure to the heat shrinkable tube and further a radial pressure to the rock sample; pumping hydraulic oil into a hydraulic flow passage of the pressure head by an axial pressure hydraulic pump; applying, by the pressure head, an axial force to the rock sample, till numerical values of a pressure gauge A, a pressure gauge B and a pressure gauge C reach experimentally set pressure values; turning off the hydraulic pump to form a stress field;
S1(5), observing the reading of the thermometer A; proceeding to the next step when a numerical value of the thermometer A is stabilized to an experimentally set numerical value;
S1(6), closing the valve Vb, opening the valve Vc, and pressurizing the constant-flux pump; pumping, by the constant-flux pump, the carbon carbonate in the second intermediate container into the experiment chamber through the valve Vc and the valve Vx in sequence; then closing the valve Vc and the valve Vx, and standing for a period of time;
S1(7), closing the valve Vg and the valve Vh after the gases in the experiment chamber are mixed sufficiently; opening the valve Vf, the valve Vm and the valve Vy, wherein the mixed gas in the experiment chamber flows out from the valve Vm according to a preset outlet pressure, and then is sprayed out from a back pressure valve; metering a volume of the gas by a gasometer, and then detecting components of the discharged gas with a gas chromatograph; during the experiment, automatically acquiring, by the axial extensometer and the radial extensometer, an axial deformation and a radial deformation of the rock sample, and transmitting the acquired data to a console;
S1(8), at the end of the experiment, recovering the tight sandstone or rock sample, sealing and stocking the unused high-purity experimental carbon dioxide, tight gas or shale gas; and restoring the device to a shutdown state;
S2, a test of displacing tight oil or shale oil with carbon dioxide under multi-field coupling, which includes the following test steps:
S2(1), preparing a tight sandstone or shale rock sample as a rock sample; compounding carbon dioxide in a fourth intermediate container, compounding tight oil or shale oil in a third intermediate container, inspecting various components of the device and their connection relationships and adjusting them to initial working states;
S2(2) repeating steps S1(2) to S1(3); then turning off the vacuum pump and closing the valve Vn; opening the valve Va, the valve Vd and the constant-flux pump; pumping, by the constant-flux pump, crude oil in the third intermediate container into the experiment chamber through the valve Vd and the valve Vx in sequence to make the rock sample saturated, i.e., the rock sample is filled with the tight oil or shale oil, thereby forming a pore pressure field and a seepage field; opening the valve Vj and the valve Vk at the same time, and introducing hydraulic oil into the experiment chamber by the confining pressure hydraulic pump; applying, by the hydraulic oil, a radial pressure to the heat shrinkable tube and further a radial pressure to the rock sample; pumping hydraulic oil to the hydraulic flow passage of the pressure head by the axial pressure hydraulic pump, such that the pressure head applies an axial force to the rock sample, till numerical values of the pressure gauge A, the pressure gauge B and the pressure gauge C reach experimentally set pressure values; turning off the hydraulic pump to form a stress field;
S2(3) repeating the step S1(5); then closing the valve Vd and the valve Vf, and opening the valve Ve, the valve Vg, the valve Vh and the valve Vm; pressurizing the constant-flux pump; pumping, by the constant-flux pump, the carbon dioxide in the fourth intermediate container into the experiment chamber through the valve Ve and the valve Vx in sequence;
S2(4) enabling testing fluid in the experiment chamber to flow out from the valve Vm and the back pressure valve according to a preset outlet pressure; after a gas-liquid mixture passes through a gas-liquid separator, metering a volume of gas by the gasometer when the gas enters the gasometer, and then detecting components of the discharged gas with a gas chromatograph; metering the volume of liquid by a liquid meter when the liquid enters the liquid meter, and detecting components of the liquid with a liquid chromatograph; during the experiment, automatically acquiring, by the axial extensometer and the radial extensometer, an axial deformation and a radial deformation of the rock sample, and transmitting the acquired data to a console;

S2(5) at the end of the experiment, recovering the tight sandstone or shale, sealing and stocking the unused high-purity experimental carbon dioxide, tight oil or shale oil; and restoring the device to a shutdown state;

S3, a test of exploitation efficiency by replacing hydrate with carbon dioxide under multi-field coupling, the step S3 includes the following steps:

S3(1), preparing a hydrate reservoir rock sample to be tested; placing methane in the first intermediate container, placing distilled water in the third intermediate container, and placing carbon dioxide in the fourth intermediate container; inspecting various components of the device and their connection relationships and adjusting them to initial working states;

S3(2) repeating the step S1(2); then closing the valve Vb, the valve Vc, the valve Vd, the valve Ve, the valve Vm and the valve Vy; opening the valve Vn, the valve Vi and the valve Vx; turning on the vacuum pump and an air conditioning oil refrigerator; vacuumizing the experiment chamber with the vacuum pump to further vacuumize the rock sample; pumping a cooling medium to a cold bath by the air conditioning oil refrigerator to refrigerate the experiment chamber, and further refrigerating the rock sample;

S3(3), when a numerical value displayed on the pressure gauge C is stable, turning off the vacuum pump, closing the valve Vn, and opening the valve Va, the valve Vb and the valve Vd; pumping, by the constant-flux pump, the methane in the first intermediate container into the experiment chamber through the valve Vb and the valve Vx in sequence, and meanwhile, pumping, by the constant-flux pump, the distilled water in the third intermediate container into the experiment chamber through the valve Vd and the valve Vx in sequence, such that the rock sample is saturated, wherein, the rock sample is filled with the methane and the distilled water; continuously cooling by the air conditioning oil refrigerator to form a stable low-temperature field; opening the valve Vj and the valve Vk at the same time; introducing, by the confining pressure hydraulic pump, hydraulic oil to the experiment chamber; applying, by the hydraulic oil, a radial pressure to the heat shrinkable tube and further a radial pressure to the rock sample; pumping, by the axial pressure hydraulic pump, hydraulic oil into the flow passage of the pressure head, such that the pressure head applies an axial force to the rock sample, till the numerical values on the pressure gauge A, the pressure gauge B, and the pressure gauge C reach the experimentally set pressure values; maintaining the set pressure values to form a stable stress field and a pore pressure field;

S3(4) repeating the step S1(5); after stable natural gas hydrate is formed inside the experiment chamber, closing the valve Vb and the valve Vd; pumping, by the constant-flux pump, the carbon dioxide in the fourth intermediate container into the experiment chamber through the valve Ve and the valve Vm in sequence; introducing a sufficient amount of carbon dioxide, and then closing the valve Va, the valve Ve and the valve Vx; standing the experiment chamber for a period of time;

S3(5), closing the valve Vf, and opening the valve Ve, the valve Vg, the valve Vh and the valve Vm; setting a pressure of the back pressure valve; enabling testing fluid in the experiment chamber to flow out from the valve Vm and the back pressure valve according to a preset outlet pressure; after a gas-liquid mixture passes through the gas-liquid separator, metering a volume of gas by the gasometer when the gas enters the gasometer, and then detecting components of the discharged gas with a gas chromatograph; metering the volume of liquid by a liquid meter when the liquid enters the liquid meter, and detecting components of the liquid with a liquid chromatograph; during the experiment, automatically acquiring, by the axial extensometer and the radial extensometer, an axial deformation and a radial deformation of the rock sample, and transmitting the acquired data to a console;

S3(6), at the end of the experiment, recovering the hydrate reservoir rock sample, sealing and stocking the unused experimental carbon dioxide, methane gas or distilled water; and restoring the device to a shutdown state;

S4, a test of heat exchange efficiency of geothermal heat under multi-field coupling, which includes the following steps:

S4(1), preparing a hot dry rock sample to be tested; compounding formation water in the third intermediate container; inspecting various components of the device and their connection relationships and adjusting them to initial working states;

S4(2), repeating the steps S1(2) to S1(3) to form a stable temperature field; then, opening the valve Vj and the valve Vk; applying, by the confining hydraulic pump, a radial force to hot dry rock, and applying, by the axial pressure hydraulic pump, an axial pressure to the hot dry rock; when the readings on the pressure gauge A, the pressure gauge B and the pressure gauge C reach stable values, forming a stable stress field; then, turning off the vacuum pump and the valve Vn, and opening the valve Va and the valve Vd; pumping, by the constant-flux pump, the formation water in the third intermediate container into the hot dry rock through the valve Vd and the valve Vx in sequence;

S4(3), opening the valve Vm, and closing the valve Vf and the valve Vh; enabling the formation water to flow out from the back pressure valve and to enter the liquid meter; metering the volume of the distilled water by the liquid meter; metering, by a thermometer C, the temperature of the formation water at the inlet end; metering, by a thermometer B, the temperature of the flowing-out formation water;

S4(4), during the experiment process, automatically acquiring an axial deformation or a radial deformation of the hot dry rock by extensometers;

S4(5), at the end of the experiment, recovering the hot dry rock, sealing and stocking the unused formation water; and restoring the device to a shutdown state.

* * * * *